United States Patent [19]

Barfod

[11] Patent Number: 4,652,758
[45] Date of Patent: Mar. 24, 1987

[54] NUCLEAR IMAGING TOMOGRAPHY
[75] Inventor: Jesper M. Barfod, Dr. Molle, Denmark
[73] Assignee: General Electric Company, Milwaukee, Wis.
[21] Appl. No.: 617,301
[22] Filed: Jun. 4, 1984
[51] Int. Cl.$^4$ .............................................. G01T 1/20
[52] U.S. Cl. ................................................ 250/363 S
[58] Field of Search ................ 250/363.2, 363.4, 363.5
[56] References Cited
U.S. PATENT DOCUMENTS
4,216,381  8/1980  Lange .................................. 250/363
4,503,331  3/1985  Kovacs, Jr. et al. ............ 250/363.5

Primary Examiner—Janice A. Howell
Attorney, Agent, or Firm—Douglas E. Stoner; Alexander M. Gerasimow

[57] ABSTRACT

In a nuclear imaging tomographic scanner, a drive mechanism is included to selectively move the patient in an axial plane to thereby maintain a close proximity to the detector for the purpose of increasing resolution. In this way, the actual movement of the camera head is in a simple circle whereas the relative movement of the camera head with respect to the patient is one wherein the detector tends to follow the general contour of the patient by the movement within an oval path.

10 Claims, 5 Drawing Figures

R = 35, d = 25, b = 20 cm

R = 35, d = 30, b = 25 cm

NUCLEAR IMAGING TOMOGRAPHY

BACKGROUND OF THE INVENTION

This invention relates generally to scintillation cameras used in nuclear medicine, and, more particularly, to nuclear camera apparatus for obtaining tomographic images.

In nuclear camera imaging, it has long been recognized that one can obtain improved image resolution and contrast by positioning the camera head as close to the organ of interest as possible. When performing planar imaging, it has been a simple matter to move the camera as close as possible to the patient to thereby allow minimum camera-to-organ distance. When performing tomographic imaging, on the other hand, the operator is not able to acquire the same proximity to the camera. That is, since the conventional tomographic camera system rotates the camera head in a circle around the longitudinal axis of the patient, the non-circular shaped cross section of the patient requires that the camera head be placed at a farther distance from the patient than desired when obtaining a coronal (front or back) view.

One approach for minimizing the patient-detector distance is that of moving the camera head in a non-circular, or generally oval path about the patient. This procedure is mechanically difficult when considering the substantial weight of a camera head. Further, even if one is able to construct a camera which will move its head in an oval pattern, it is difficult to include the flexibility to accommodate different-sized ovals so as to satisfactorily accommodate different-sized patients.

Another problem arises with the concept of moving the camera in an oval pattern around the patient. If the camera head is cantilevered from a longitudinally displaced position with respect to the patient, as it most commonly is, then any radial movement of the camera head which is necessary to obtain an oval path will also result in an associated axial movement of the camera with respect to the patient. This, in turn, tends to restrict the camera's field of view, since the part of the patient that the camera sees will vary as the rotation occurs. Although provision can be made to correct for the change in the detector axial position as the data is collected, this correction may result in a degradation of resolution. Further, it must be recognized that the organs of interest, such as the liver or the lungs, may not be entirely within the field of view during the entire camera rotation, thereby necessarily degrading the resolution of any resulting image.

It is therefore an object of the present invention to provide a nuclear imaging tomography system with improved image resolution and contrast.

Yet another object of the present invention is the provision in a nuclear imaging tomography system for minimizing the patient-detector distance as the camera is moved around the patient to obtain the various views for reconstruction.

Still another object of the present invention is the provision for a nuclear imaging tomography system which minimizes the patient-detector distance while maintaining a full field of view during the rotation around the patient.

Yet another object of the present invention is the provision for a nuclear imaging tomography system which is economical to manufacture and practical in use.

These objects and other features and advantages become more readily apparent upon reference to the following description when taken in conjunction with the appended drawings.

SUMMARY OF THE INVENTION

Briefly, in accordance with one aspect of the invention, the camera head of a tomographic apparatus is rotated around the patient in a circular orbit while the patient-supporting table is synchronously moved in a transverse plane to thereby cause the relative movement of the camera head about the patient to be in an oval or generally elliptical pattern. In this way, the relatively simple circular pattern is maintained for the heavy camera while the accommodating relative movement can be accomplished with a simple movement of the table. The camera-to-patient distance is thus maintained close to a minimum at all positions around the patient. Further, the center of the oval, or another point fixed in relation to the patient, will be imaged on the center of the detector such that a full field of view will be maintained in all positions around the patient.

By another aspect of the invention, the two-dimensional movement of the table can be programmed to vary the size of the oval or ellipse as desired to accommodate the size of the patient. This is accomplished by first defining the parameters of the patient/table combination and then establishing the two-dimensional coordinates of the necessary table movement accordingly.

In the drawings hereinafter described, a preferred embodiment is depicted; however, various other modifications and alternate cnstructions can be made thereto, not departing from the true spirit and scope of the invention.

DESCRIPTION OF THE PREFERRED EMBODIMENT

Figure 1:
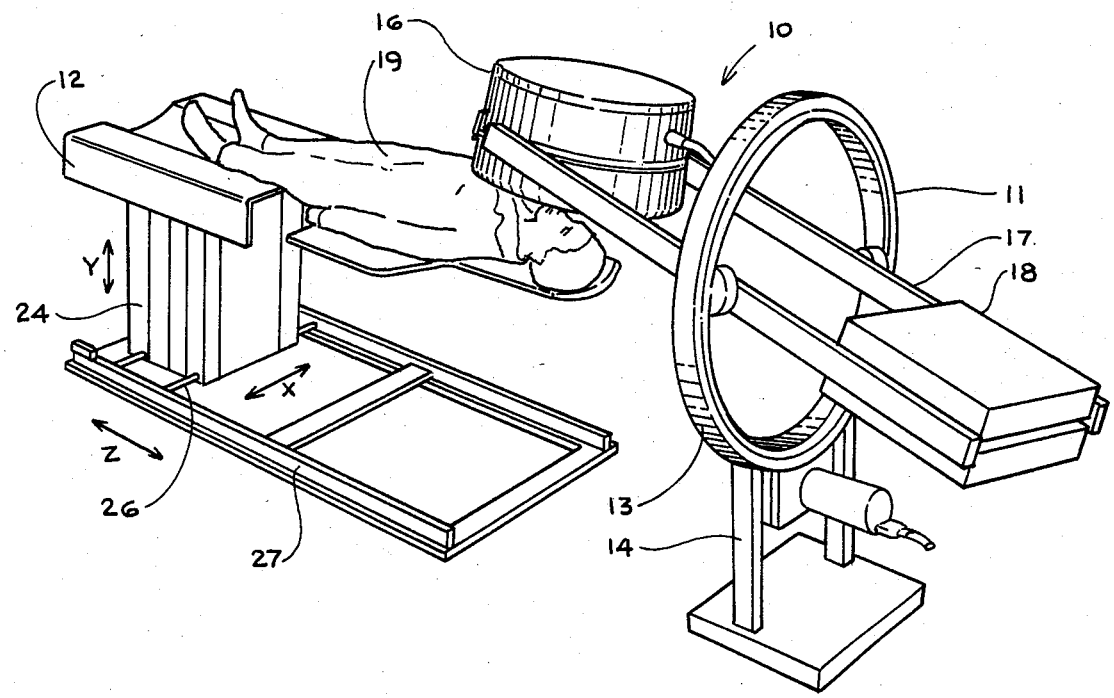
FIG. 1 is a perspective view of the nuclear imaging tomography system having the invention incorporated therein.

Referring now to FIG. 1, there is shown, generally at 10, a nuclear imaging tomographic scanning system which includes a tomographic scanner 11, and a patient support table 12. The construction and operation of the scanner 11 is similar to that shown and described in U.S. Pat. No. 4,216,381, issued on Aug. 5, 1980, and assigned to the assignee of the present invention. Briefly, the scanner 11 comprises an annular gantry 13 supported in a vertical position as shown by a pedestal 14 and having a camera head 16 supported from the gantry 13 in cantilevered fashion by an arm assembly 17 and balanced by a counterweight 18 on the other end of the arm assembly 17. The arm assembly 17 is so connected to the gantry 13 as to allow the entire arm assembly 17 to be rotated within the gantry 13 by a motor-drive system (not shown), to thereby rotate the camera head 16 in a circular path around the patient 19 supported on the table 12 for the purpose of gathering data which can be used to reconstruct a tomographic image of the patient in the area of concern. The structure and operational movement of the scanner 11 is of a conventional nature in this regard.

Recognizing the desirability for close proximity and the difficulty with the concept of moving the camera head in an elliptical path, the present invention is designed to obtain an effective elliptical path of the camera head 16 around the patient 19 but without the mechanical complications of moving the heavy camera head 16 radially in and out, and without the introduction of the complications brought about by the misalignment of the patient 19 with respect to the camera head 16. This is accomplished by maintaining a circular orbit with the camera head 16 while synchronously moving the patient support table 12 in the transverse axial plane (i.e., both vertically and horizontally) to obtain an effective elliptical path of the camera head 16 around the patient 19.

Figure 2:
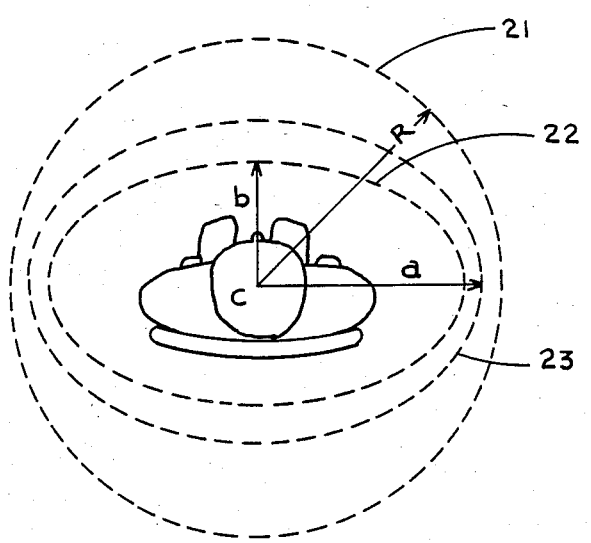
FIG. 2 is a schematic illustration of various positional parameters in accordance with the preferred embodiment of the invention.

The relative position of the camera with respect to the patient is illustrated in FIG. 2 wherein the dashed line 21 is representative of the circular orbit of the camera head 16 about a center C on the longitudinal axis. The radius R can be varied to accommodate the size of the patient, but once chosen, remains constant throughout a particular scan. In another approach, the radius R remains fixed at a predetermined distance for all patients, with the different sized patients being accommodated by table movement alone. For the purpose of determining the amount of table movement in accordance with the inventive concept, the shape of the patient-and-table combination is represented by an ellipse indicated by the dotted line 22. That ellipse is defined by the dimensions "a" and "b" as shown, which are in turn determined by the size of the patient.

The patient-support table 12 is designed so that it can be moved both horizontally and vertically in such a manner that the relative position of the camera head 16 with respect to the center C (as that point C moves with the table) is defined by the dotted line ellipse indicated at 23 in FIG. 2. The required horizontal and vertical movement of the table can be calculated as follows:

$$(X) = \cos\theta(R - \sqrt{a^2\cos^2\theta + b^2\sin^2\theta})$$ Equation (1)

$$(Y) = \sin\theta(R - \sqrt{a^2\cos^2\theta + b^2\sin^2\theta})$$ Equation (2)

Where
$\theta$ is projection angle of the camera head during its rotation
R is radius of rotation of the camera head
a is horizontal half axis of the patient/table defining ellipse
b is vertical half axis of the patient/table defining ellipse With respect to the movement of the table 12, reference is again made to FIG. 1 wherein the table 12 is shown to be mounted on a moveable base 24, which in turn is movably mounted on a pair of transverse rods 26. A motor (not shown) is provided in the base and is connected to an appropriate drive means, such as a mechanical linkage, a hydraulic piston, or the like, to selectively move the base 24 on the transverse rods 26 in the X direction as shown. Similarly, another motor means is provided to move the table 12 in the Y direction as shown. In this way provision is made to selectively position the table 12 closer to the camera head 16 as the camera head rotates around the patient.

Provision is also made to selectively move the entire assembly (i.e., the table 12, the base 24, and the transverse rods 26) longitudinally in the Z direction. This movement is useful not only for obtaining full-body scans in a conventional manner but also in selectively positioning the patient 19 in the desired longitudinal position for purposes of tomographic examinations. However, it should be pointed out that during the process of a single scan, the table is not moved in the longitudinal direction, but rather only in the vertical and horizontal directions.

Figure 3A:
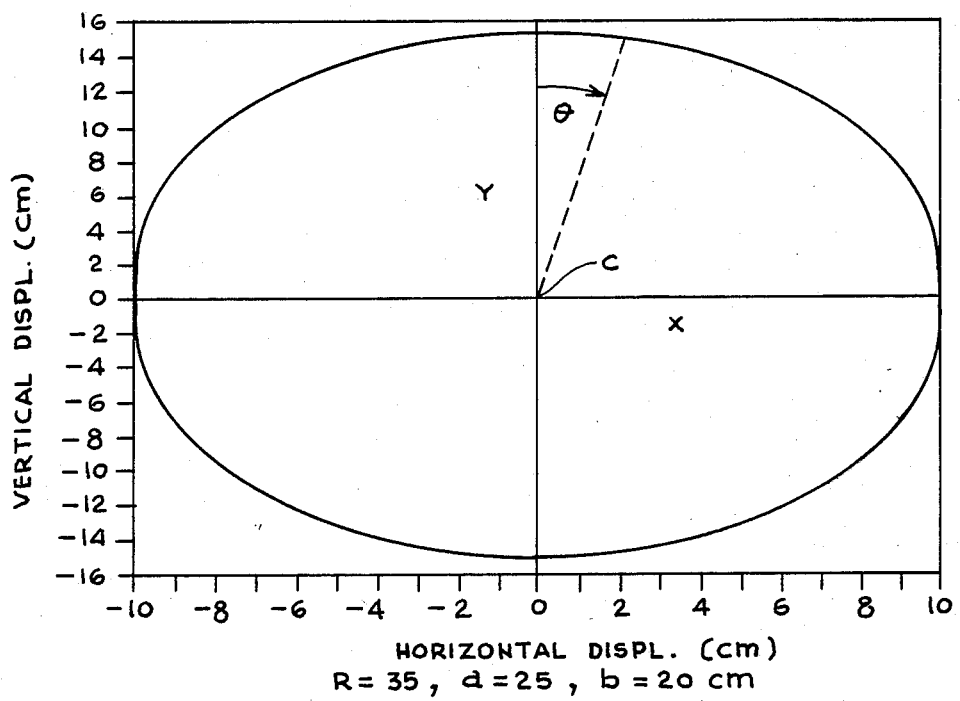
FIGS. 3a and 3b are graphic illustrations of the table movement in accordance with the preferred embodiment of the invention.
Figure 3B:
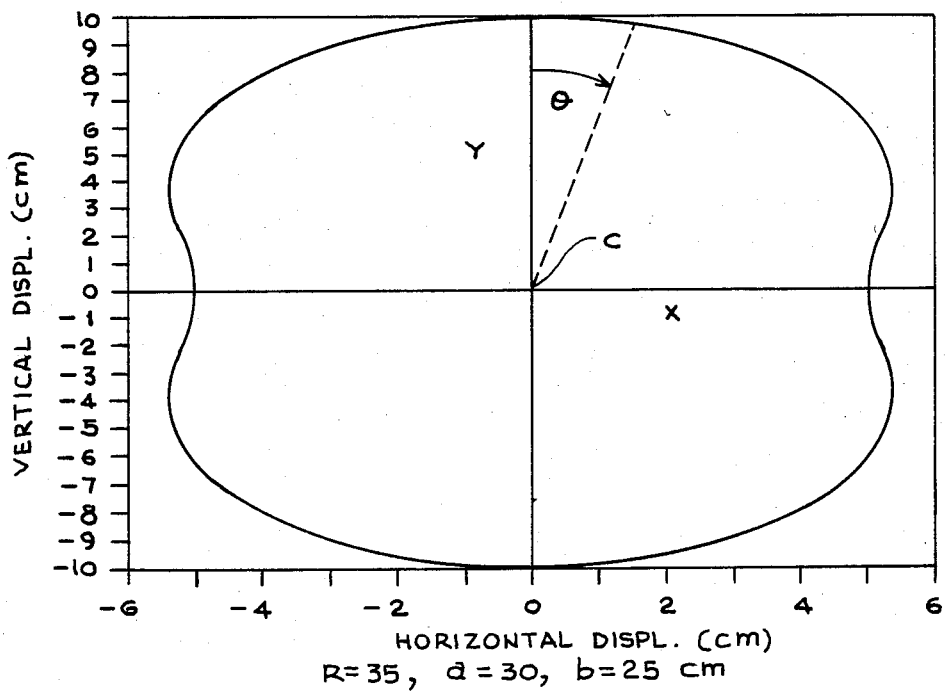

Referring now to FIGS. 3a and 3b, there are shown two graphs which illustrate representative table movement schedules for scans to be made in accordance with the present invention. The X and Y values are calculated with the use of Equations (1) and (2) set forth above. It should be pointed out that, as shown, the X and Y coordinates are of different scale and therefore the actual table movement will not be the same as that traced in the graphic plot. For example, in FIG. 3a, it would appear that the locus of the table position is close to a horizontally disposed ellipse, whereas in fact, the actual locus represents more closely a vertically disposed ellipse. However, the actual path of table movement will not necessarily, or even likely, be in an elliptical pattern. For example, as will be seen in FIG. 3b, the path of table movement when the camera is near the side of the table is somewhat irregular because of a rather unique mathematical relationship between the radius of rotation and the horizontal and vertical axes of the elliptical patient shape.

As suggested above, the particular table movement pattern for a given scan will depend on the size of the patient. The patient's size will in turn determine the radius of camera rotation R, and the "a" and "b" coordinates of the ellipse which approximates the shape of the patient/table combination. In FIGS. 3a and 3b the same radius of rotation (i.e. R=35 cm) is used in both; however, the parameters "a" and "b" of the size-defining ellipse are different, thereby reflecting a larger patient in the case of the FIG. 3b scan.

Figure 4:
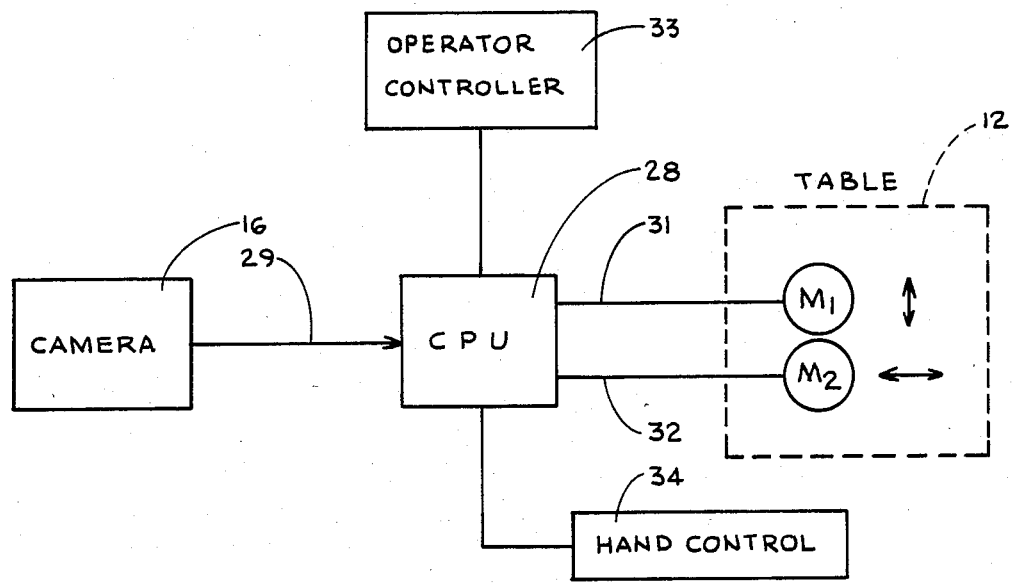
FIG. 4 is a schematic illustration of the positional control mechanism in accordance with the preferred embodiment of the invention.

The system for controlling the movement of the patient table is shown schematically in FIG. 4. A central processing unit CPU or controller 28 is provided to monitor and control the positions of the patient-support table 12 and of the camera head 16. The position of the camera 16 at any particular instant is provided to the CPU 28 by way of line 29. This position can be determined by the use of potentiometers or the like to provide (1) an electrical signal to indicate the angulation of the arm assembly 17 to thereby provide an indication of the radius R, as well (2) as a signal representation of the rotational position O of the arm assembly 17 within the gantry 13.

Movement of the table 12 is brought about by a vertical control motor M-1 and a horizontal control motor M-2, which communicate with the CPU 28 by lines 31 and 32, respectively. The CPU 28 also communicates with the central operator controller 33 and a hand-controlled device 34.

In operation, the patient is placed on the support table 12 in preparation for a scan. The camera head 16 is then moved by way of the hand control 34 to various positions around, and in close proximity to, the patient. In this way, the relevant parameters (i.e., the Radius and the "a" and "b" dimensions) can be measured for establishing the desired operating parameters. For a given set of R, "a", and "b" parameters, the desired X and Y values for movement of the table in synchrony with the rotation of the camera head 16 around the gantry 13 can be calculated with the use of the equations (1) and (2) above.

It will be understood that the present invention has been described in terms of a preferred embodiment, but may take any number of other forms while remaining within the scope and intent of the invention. For example, although the pattern of relative movement of the camera head around the patient has been descried in terms of an oval or elliptical shape, the table movement can be made to accommodate any desired shape.

In the above-described invention, what is claimed as novel and desired to be secured by Letters Patent in the United States is:

1. An improved tomographic imaging apparatus of the type having a scintillation detector which is adapted to revolve around a table supported patient for the purpose of obtaining multiple views of the patient for the reconstruction of an axial image comprising: means for moving the table in two dimensions in the plane of the detector motion and in synchrony with the revolving of the detector such that the distance between the patient and the detector is minimized.

2. An improved tomographic imaging apparatus as set forth in claim 1 wherein said table moving means also comprises means for moving the table in a plane transverse to the longitudinal axis of the table.

3. An improved tomographic imaging apparatus as set forth in claim 1, wherein said table moving means includes a pair of motors for moving the table in the vertical and horizontal directions, respectively.

4. An improved tomographic imaging apparatus as set forth in claim 1 wherein said table moving means is operative to move the table in such a pattern that the relative position of the detector with respect to the patient traces a generally oval pattern.

5. A method of scanning an object with a scintillation detector for the purpose of reconstructing a tomographic image comprising the steps of: (a.) Rotating a scintillation detector in a circular path in a plane and intersecting a longitudinal axis of the object while maintaining the center of the detector aligned with a fixed point in the object; and (b.) synchronously moving the object in two dimensions of said plane to continuously maintain a minimum distance between the object and the detector.

6. A method of scanning as set forth in claim 5 wherein the object-moving step is accomplished in such a manner as to relatively move the detector in an oval pattern around the object.

7. A method of scanning as set forth in claim 5 and including the steps of gathering information from the detector during its rotation cycle and processing that data to obtain a tomographic image of the object.

8. A tomographic scanner of the type having a radiation detector for rotation around a longitudinal axis to detect radiation at discrete positions around an included object for the purpose of reconstructing a tomographic image of a transverse slice of the object comprising:
means for rotating the detector in a circle centered in the longitudinal axis; and
means for synchronously moving the object in two dimensions within the plane of the transverse slice such that the detector tends to follow the general contour of the object's outer shape while tending to remain in close proximity to the object as the detector rotates around the object.

9. A tomographic scanner as set forth in claim 8 wherein said object moving means comprises a pair of motors which are connected to a table-movement mechanism, with one motor adapted to move the table in the vertical direction and the other motor adapted to move the table in the horizontal direction.

10. A tomographic scanner as set forth in claim 8 wherein the means for synchronously moving the object moves the object such that a fixed point within the object remains aligned with the center of said detector during the entirety of the rotation of said detector around the longitudinal axis.

* * * * *